United States Patent [19]

Buelna et al.

[11] Patent Number: 5,605,539
[45] Date of Patent: Feb. 25, 1997

[54] SELF-INTRODUCING INFUSION CATHETER

[75] Inventors: Terry Buelna, Long Beach; Wayne A. Noda, Mission Viejo, both of Calif.

[73] Assignee: Urohealth Systems, Inc., Costa Mesa, Calif.

[21] Appl. No.: 241,953

[22] Filed: May 12, 1994

Related U.S. Application Data

[63] Continuation of Ser. No. 943,808, Sep. 11, 1992, abandoned.
[51] Int. Cl.⁶ .................................................. A61M 1/00
[52] U.S. Cl. ........................... 604/51; 604/21; 606/37; 606/40; 606/49
[58] Field of Search ............................ 604/20, 21, 22, 604/28, 53, 51; 606/35, 36, 37, 38, 39, 45, 46, 40, 49

[56] References Cited

U.S. PATENT DOCUMENTS

| | | | |
|---|---|---|---|
| 3,595,239 | 7/1971 | Petersen | 606/45 |
| 3,918,456 | 11/1975 | Patel | 128/348 |
| 4,306,566 | 12/1981 | Sinko | 128/658 |
| 4,547,187 | 11/1985 | Kelly | 604/49 |
| 4,562,838 | 1/1986 | Walker | 604/22 |
| 4,641,649 | 2/1987 | Walinsky et al. | 128/303 |
| 4,682,596 | 7/1987 | Bales et al. | 606/45 |
| 4,785,815 | 11/1988 | Cohen | 128/642 |
| 4,836,211 | 6/1989 | Sekino et al. | 128/662 |
| 4,870,953 | 10/1989 | Donmicheal et al. | 128/24 |
| 4,936,281 | 6/1990 | Stasz | 604/22 |
| 4,967,765 | 11/1990 | Turner et al. | 128/785 |
| 4,979,948 | 12/1990 | Geddes et al. | 606/33 |
| 4,998,933 | 3/1991 | Eggers et al. | 606/41 |
| 5,071,412 | 12/1991 | Noda | 604/268 |
| 5,080,660 | 1/1992 | Buelna | 606/49 |
| 5,083,565 | 1/1992 | Parins . | |
| 5,083,568 | 1/1992 | Parins | 128/642 |
| 5,186,714 | 2/1993 | Boudreault et al. | 604/33 |
| 5,195,958 | 3/1993 | Phillips | 606/40 |
| 5,195,959 | 3/1993 | Smith | 606/49 |
| 5,197,963 | 3/1993 | Parins | 606/50 |
| 5,207,675 | 5/1993 | Canady | 606/49 |
| 5,267,994 | 12/1993 | Gentelia et al. | 606/45 |
| 5,273,524 | 12/1993 | Fox et al. | 604/21 |
| 5,300,069 | 4/1994 | Hunsberger et al. | 606/37 |
| 5,342,357 | 8/1994 | Nardella | 606/38 |

*Primary Examiner*—Corrine M. McDermott
*Assistant Examiner*—N. Kent Gring
*Attorney, Agent, or Firm*—Burns, Doane, Swecker & Mathis, L.L.P.

[57] ABSTRACT

A self-introducing infusion catheter comprises a substantially rigid, elongate shaft having a longitudinal passage therethrough and an infusion port at its distal end. An electrode is further mounted at the distal end. The electrode is electrically coupled to a connector at the proximal end of the shaft which may be connected to an electrosurgical power supply. The connector is further in communication with the passage in the shaft and provides fluid connection with an infusion fluid delivery device. In the method of the invention, the catheter is connected to an electrosurgical power supply and ablative energy is applied to abdominal tissue through the electrode. This facilitates penetration of the tissue to position the device in the abdominal cavity through the abdominal wall. The distal end of the catheter is positioned through an incision in a body structure, such as the cystic duct, and the proximal end is connected to an infusion fluid delivery device. The distal end is clamped in position in the duct, and an infusion fluid such as contrast medium is infused into the duct.

11 Claims, 4 Drawing Sheets

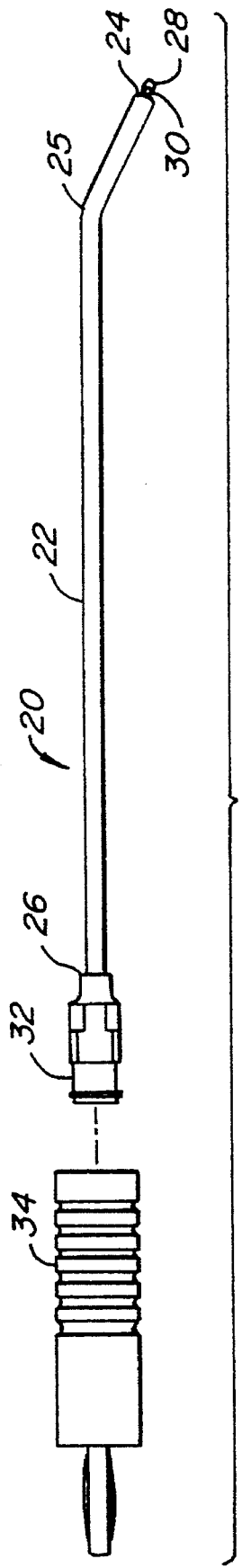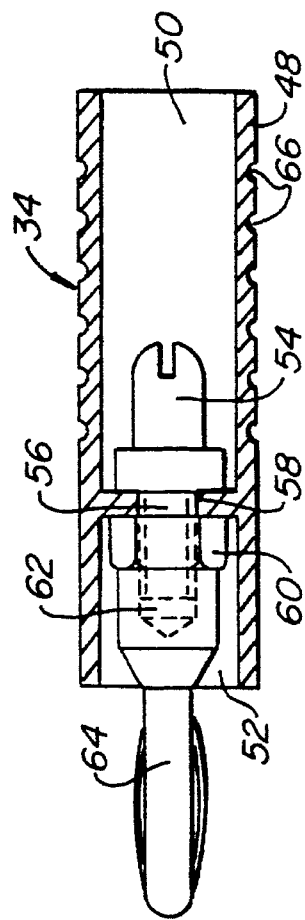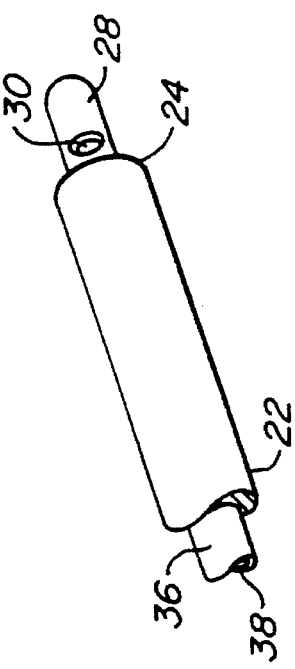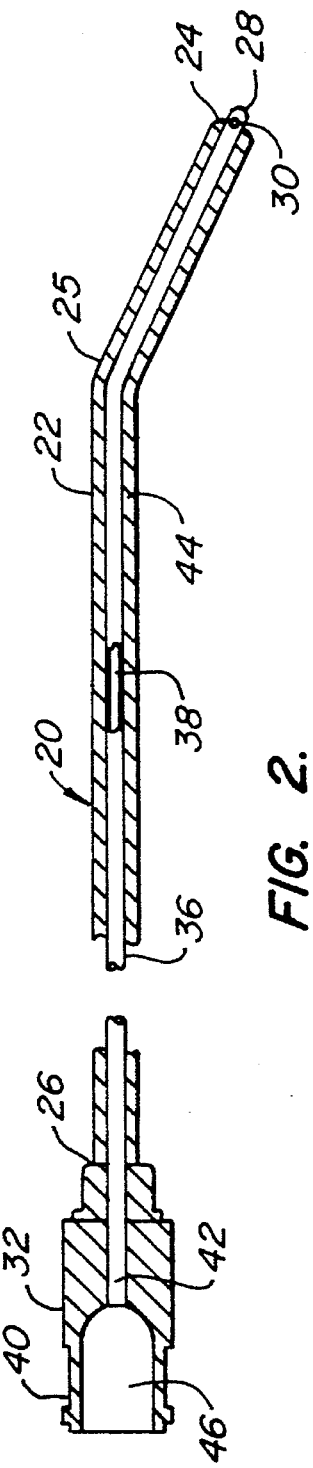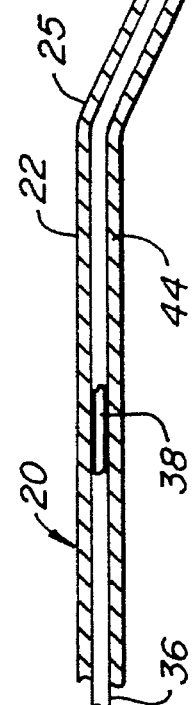

SELF-INTRODUCING INFUSION CATHETER

This is a Continuation of application Ser. No. 07/943,808, filed Sep. 11, 1992, now abandoned.

BACKGROUND OF THE INVENTION

1. Field of the Invention

The present invention relates generally to the structure and use of surgical instruments. More particularly, the present invention relates to a device and method for introducing a fluid, such as contrast medium, to a body duct, such as the cystic duct.

Cholangiography is a procedure for the X-ray of a patient's bile duct which is commonly performed to locate duct stones during surgical gallbladder removal. The presence of gallstones in the biliary ducts, particularly the common bile duct, is a painful and potentially fatal condition which exists in a significant percentage of patients who have undergone gallbladder removal. Surgical exploration of the common bile duct, however, is itself a relatively risky procedure which is associated with significant morbidity. Thus, the ability to locate the presence of gallstones by cholangiography is of significant benefit to the patient.

Surgical gallbladder removal, referred to as cholecystectomy, is most commonly performed as an open surgical procedure through a major incision in the patient's abdomen. After the gallbladder is removed, and the cystic duct ligated, a flexible catheter is introduced through a small incision in either the cystic duct or the common bile duct. A suitable contrast medium may then be introduced through the catheter to permit X-ray detection of any gallstones which may be present in the ducts.

Cholecystectomy and cholangiography are being performed with increasing frequency using laparoscopic surgical techniques. Laparoscopic surgery is performed through small incisions in the patient's abdomen allowing the necessary surgical instruments to be introduced through a tube, such as a cannula, while the physician observes manipulation of the instruments through a laparoscope. Such laparoscopic surgery offers significant advantages over conventional "open" cholecystectomy and cholangiography. In particular, the laparoscopic technique is usually less traumatic, requires a shorter recovery time, and is significantly less costly than the corresponding open surgical procedure.

The performance of laparoscopic cholangiography is not without its problems, however. A significant drawback is the need to position a cannula as an accessway through the abdominal wall for every instrument to be used during the procedure. The use of a large number of cannulas inflicts an undesirable degree of trauma on the patient. Further, it may be difficult to accurately predict the locations in the abdomen which will provide the most convenient points of access to the surgical site. If a cannula is positioned at an inconvenient location, it must be removed and repositioned, or an additional cannula must be inserted at the desired location, increasing traumatic impact. Trauma is worsened by the size of the cannulas used in laparoscopic procedures. Known cannulas tend to have an undesirably large diameter due to the need to provide a sealed access port of sufficient diameter to accommodate the laparoscopic instruments used in cholecystectomy and/or cholangiography procedure. Moreover, known cannulas require the use of specialized introduction instruments, such as needles or obturators, for percutaneous insertion through the abdominal wall.

For these reasons, it would be desirable to provide improved devices and methods to facilitate the introduction of fluids, such as contrast media, to body ducts, such as the biliary ducts. It would be particularly desirable to provide instruments for performing cholangiography using laparoscopic and other "least invasive surgical" procedures which would reduce the number of cannulas needed for access to the surgical site. Most desirably, the instruments should be self-introducing, without requiring the use of separate needles, obturators or other introduction instruments, and should not need cannulas or other such devices for percutaneous access to the surgical site. The devices should have a small cross-section to minimize traumatic impact. The device and method should further allow infusion of fluid in a single direction within a duct, and prevent fluid flow in undesired directions in the duct or leakage out of the duct.

2. Description of the Background Art

Catheters and cannulas for introducing contrast media to a patient's bile ducts following open surgical gall bladder removal are described in the patent and medical literature. See, for example, U.S. Pat. Nos. 4,747,823; 4,547,187; 4,306,566; 4,044,757; 4,044,7581; and 3,918,456. Devices for clamping the cystic duct in conjunction with the open surgical introduction of a cholangiogram catheter are described in U.S. Pat. Nos. 4,817,604 and 4,792,330.

SUMMARY OF THE INVENTION

The present invention provides improved devices and methods for introducing fluids to the lumen of a body duct. The devices and methods are particularly well-suited to use in laparoscopic and other least invasive surgical procedures. Traumatic impact upon the patient is significantly reduced using the devices and methods of the invention. This is achieved by providing the capability for self-introduction, by eliminating the need for cannulas or other such access devices, and by the use of instruments having small cross-section. The devices and methods facilitate percutaneous positioning as well as infusion of a lumen of a body duct using the same self-contained instrument. The devices and methods of the present invention are especially well-adapted for performing cholangiography, and facilitate positioning an infusion port within the cystic duct and infusing a contrast medium in the duct using fewer instruments, having reduced traumatic impact and with improved positionability.

In a preferred embodiment of the present invention, a self-introducing infusion catheter comprises a catheter body with a passage therethrough, an infusion port at the distal end of the catheter body in communication with the passage, an electrode disposed at the distal end of the catheter body, and means at the proximal end of the catheter body for connecting the electrode to an energy source. The electrode is configured to apply ablative energy sufficient to facilitate penetration of tissue. The catheter body is generally rigid, having sufficient column strength such that it will not significantly deflect, fold or collapse when a axially-directed force is applied so as to penetrate tissue.

The catheter body comprises, in a preferred embodiment, an electrically conductive tube having a passage therethrough, and an insulative sleeve disposed about the tube, the sleeve having an opening at its distal end leaving a portion of the tube exposed. A proximal end of the tube will preferably be connectable to an electrosurgical power supply, such that power will be conducted through the tube to the exposed distal end. Usually, the proximal end of the tube will have a connector which may be removably connected to either an electrosurgical connector or an infusion fluid delivery device (e.g. syringe). The connector will provide electrical connection with the tube, as well as fluid connection with the lumen. In this way, the catheter may be used for percutaneous self-introduction by connection to an electrosurgical power supply, and, after introduction, the electrosurgical connector exchanged with an infusion fluid delivery device to perform cholangiography.

The infusion port at the distal end of the catheter body may comprise, in one embodiment, a distally-oriented opening in the tube in communication with the lumen. Alternatively, one or more laterally oriented openings may be provided in the tube, with or without a distal opening.

In alternative embodiments, the catheter body will comprise a tube, usually of an insulative material, having a first lumen for communicating an infusion fluid and a second lumen for housing an electrode wire. An electrode will be mounted at the distal end of the tube, with an electrode wire extending through the second lumen to the proximal end of the catheter body and connected to an electrosurgical connector. The proximal end of the tube may include an interchangeable connector for removable connection to an electrosurgical connector or an infusion fluid delivery device. Alternatively, the proximal end may have a permanently-mounted electrosurgical connector and a separate fitting for connection to an infusion fluid delivery device.

Usually, the electrosurgical power supply will comprise a radiofrequency (RF) power generator, but alternative types of energy may be used, including ultrasound and the like. The electrosurgical power supply will deliver energy at power levels sufficient to ablate tissue for penetration of the skin so as to facilitate self-introduction of the infusion catheter.

In a preferred aspect of the method of the present invention, a catheter is percutaneously introduced by applying energy to body tissue through an electrode disposed at the distal end of the catheter, the energy being sufficient to ablate tissue to penetrate into a body cavity. After introduction, a distal portion of the catheter is positioned through an opening in a wall of a body duct such that an infusion port in the distal portion is within the duct. A surgical clip may be applied about the periphery of the duct to secure the catheter in position and seal the duct against the body of the catheter. An infusion fluid is then infused through the infusion port into the body duct, the clip preventing flow of fluid out of the incision or in an undesired direction in the duct.

In an exemplary embodiment, the method will be used for purposes of cholangiography, wherein the body duct will usually be the cystic duct and the infusion fluid will be a contrast medium.

In a further aspect of the method of the present invention, the opening in the body duct through which the catheter is inserted will be made by the catheter itself. The electrode at the distal end of the catheter will be used to apply energy to the wall of the body duct so as to ablatively penetrate through the wall tissue.

A further understanding of the nature and advantages of the invention may be realized by reference to the remaining portions of the specification and the drawings.

DESCRIPTION OF THE DRAWINGS

FIG. 1 is a side elevational view of a self-introducing infusion catheter constructed in accordance with the principles of the present invention, with an electrosurgical connector separated therefrom.

FIG. 1A is a detailed perspective view of the distal end of the catheter of FIG. 1.

FIG. 2 is a side cross-sectional view of the infusion catheter of FIG. 1 without the electrosurgical connector.

FIG. 3 is a side cross-sectional view of the electrosurgical connector of FIG. 1.

DESCRIPTION OF SPECIFIC EMBODIMENTS

Figure 4A:
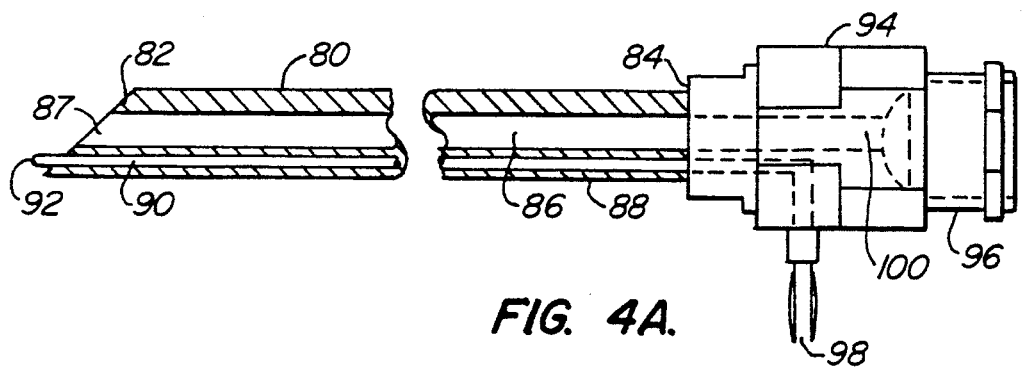
FIG. 4A is a side cross-sectional view of an alternative embodiment of a self-introducing infusion catheter constructed in accordance with the principles of the present invention.

The device and method of the present invention are useful for introducing fluids, such as contrast media, to a variety of body ducts, such as the cystic duct, bile duct, pancreatic duct, hepatic duct, uterine tube, ureter, blood vessels, and the like. The present invention is particularly useful for introducing contrast media as part of performing an X-ray imaging procedure, such as a cholangiogram, arteriograph, veinograph, ureterography, pancreatograph, and the like. While any of these procedures might be performed in conjunction with open surgery, the present invention will find its greatest use in the performance of laparoscopic, arthroscopic, and endoscopic procedures. The device and method of the present invention will find perhaps their greatest use in performing cholangiograms in conjunction with laparoscopic gallbladder removal procedures.

The device of the present invention comprises an elongate shaft having proximal and distal ends. The elongate shaft will usually have a circular cross-section, more usually comprising a cylindrical tube having an axial passage extending from the proximal to distal end. The dimensions of the shaft are not critical, but the diameter will usually be in the range from about 1 to 2 millimeters or less, in diameter. The length of the shaft will be sufficient to permit the distal end to reach any desired location in the body with the proximal end remaining external to the body, typically having a length in the range from about 10 centimeters to 15 centimeters. The shaft will be generally rigid, having sufficient column strength to allow a distal force to be exerted from the proximal end for tissue penetration without undue deflection of the distal end. The shaft will typically be formed from a rigid metal and/or plastic material, preferably with an anti-reflective coating. The distal end of the shaft may conveniently be formed in a sharpened tip to aid in penetrating tissue.

At least one electrode will be disposed at the distal end of the shaft. The electrode will be electrically coupled to a connector at the proximal end of the shaft. In a preferred embodiment, the shaft will comprise an electrically conductive tube with an insulative sleeve disposed about the tube. In a preferred embodiment, the tube is stainless steel while the sleeve is teflon. The sleeve will terminate short of the distal end of the tube, leaving a distal tip of the tube exposed. In this way the distal tip of the tube will function as an electrode. The proximal end of the tube will be connected to an electrosurgical connector.

In an alternative embodiment, the shaft will have a first passage for communicating an infusion fluid and a second passage for housing an electrode wire. In this embodiment, the shaft will usually be non-conductive, and the electrode will be mounted to its distal end with the electrode wire extending proximally therefrom in the second passage.

The electrode will be connectable to an electrosurgical power supply at the proximal end of the shaft. Usually, the power supply will comprise a radiofrequency (RF) power generator, but may also be an ultrasound energy source or other type of power supply. The power supply will preferably deliver energy at sufficient power levels to ablate tissue so as to facilitate penetration of the skin and other tissue for percutaneous introduction of the catheter.

An infusion port will be disposed at the distal end of the shaft, the infusion port being in fluid communication with a passage through the shaft. The infusion port may comprise a distally-oriented opening in the shaft and/or one or more laterally oriented openings in fluid connection with the lumen. The proximal end of the shaft will be connectable to an infusion fluid delivery device to supply infusion fluid to the passage.

The proximal end of the shaft will have, in a preferred embodiment, connections for an electrosurgical power supply and for an infusion fluid delivery device (e.g. syringe). Preferably, a single multi-purpose connector will be provided to which either an electrosurgical connector or an infusion fluid delivery device may be interchangeably connected. In this embodiment, the connector will provide both electrical connection to the electrode as well as fluid connection to the passage in the shaft. Alternatively, separate dedicated connectors may be provided, one in fluid connection with the passage in the shaft, and a second in electrical connection with the electrode.

Referring now to the figures, a number of specific constructions of the devices of the present invention will be described. While each of these constructions may contain features which are particularly useful and which may be preferred aspects of the present invention, it should be appreciated that the specific designs are not meant to be limiting and that the scope of the present invention is more accurately set forth in the preceding paragraphs and in the claims.

Referring in particular to FIGS. 1–4, a self-introducing infusion catheter 20 comprises, in a preferred embodiment, an elongate shaft or body 22 having a distal end 24 and a proximal end 26. An electrode 28 is disposed at the distal end 24, along with one or more infusion ports 30. A connector 32 is mounted at proximal end 26, to which an electrosurgical connector 34 may be connected. Connector 32 will usually be of standard design to facilitate connection to various devices, including infusion fluid delivery devices, as described more fully below. Catheter shaft 22 will preferably have a distal portion 27 extending at an angle from a bend 25 to facilitate alignment of the distal portion with a body structure to be infused, as will be described in detail below.

FIG. 1A illustrates the distal end 22 of catheter shaft 22 in greater detail. It can be seen that electrode 28 comprises the distal end of a conductive tube 36 having a passage 38 therethrough. Infusion ports 30 comprise laterally-oriented openings in tube 36 in fluid communication with passage 38. In a preferred embodiment, at least two infusion ports 30 on different sides of tube 36 will be provided.

Referring now to FIG. 2, tube 36 forms the core of shaft 22 and extends to the proximal end 26 where it is attached to connector 32. Tube 36 will be a rigid, conductive material, such as stainless steel. Surrounding tube 36 is an insulative sleeve 44 extending from proximal end 26 to a point just short of the distal end of tube 36, thereby leaving the distal tip 28 of tube 36 exposed to provide an electrode. Sleeve 44 preferably comprises an insulative, low-friction, semi-compressible material, such as Teflon™.

Connector 32 has a fitting 40 on its proximal end, which will typically comprise a standard medical luer-type fitting or other standard fitting in widespread use. In the figure, fitting 40 is shown as a female luer fitting. Connector 32 will have a passage 42 through a central portion thereof in fluid communication with passage 38 of tube 36. A proximal aperture 46 within fitting 40 is in communication with passage 40 and accommodates a hub of the complementary fitting (such as that of electrosurgical connector 34) to which connector 32 may be connected. Preferably, connector 32 will be a rigid, conductive material, and will usually be stainless steel. In this way, connector 32 provides electrical connection to conductive tube 36 (and therefore to electrode 28), as well as fluid communication to passage 38 (and therefore to infusion ports 30).

FIG. 3 illustrates the electrosurgical connector 34 which is connectable to connector 32 of infusion catheter 20. Electrosurgical connector 34 includes an insulative housing 48, typically of polycarbonate, having a distal aperture 50 and a proximal aperture 52. A male luer fitting 54, usually of a conductive material such as stainless steel, is mounted within distal aperture 50, fitting 54 having a threaded shank 56 extending proximally through an opening 58 into proximal aperture 52. A nut 60 is threaded on shank 56 to secure fitting 54 in place. A proximal end 62 of shank 56 is attached to an electrosurgical plug 64 by threads and/or adhesive to provide electrical connection therebetween. Electrosurgical plug 64 will preferably be of standard configuration for connection to a conventional electrosurgical power supply. Grooves 66 on the exterior surface of housing 48 provide improved grip on the device during use.

Electrosurgical connector 34 is connected to catheter body 22 by inserting female luer fitting 40 on connector 32 into distal aperture 50 of electrosurgical connector 34. Male luer fitting 54 is received in aperture 46 in female fitting 40 to provide rigid structural connection with catheter body 22, as well as electrical connection between electrosurgical plug 64 and conductive tube 36.

Connector 32 further facilitates connection to an infusion fluid delivery device of conventional construction. In one embodiment, as illustrated in FIGS. 5B and 5C, the infusion fluid delivery device 68 will comprise one or more syringes 70 coupled by a valve 72 to a connection line 74 having on its end a male luer fitting 76 like fitting 54 of electrosurgical connector 34. Fittings 40, 76 will provide a sealed fluid connection between the infusion fluid delivery device 68 and catheter 20. As will be described in greater detail below, infusion fluid is delivered into aperture 46 and passage 42 of connector 32, for communication to infusion ports 30 via passage 38.

Figure 4B:
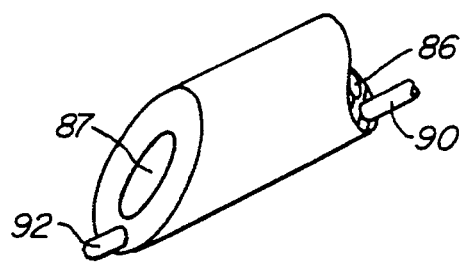
FIG. 4B is a detailed perspective view of the distal end of the infusion catheter of FIG. 4A.

An alternative embodiment of the infusion catheter of the present invention is illustrated in FIGS. 4A and 4B. In this embodiment, catheter shaft 80 is constructed of a rigid non-conductive material, usually plastic, and has a distal end 82 and proximal end 84. A first passage 86 through shaft 80 provides for communication of an infusion fluid, while a second passage 88 houses an electrode wire 90. First passage 86 has an infusion port 87 at its distal end. An electrode 92 is attached to distal end 82 of catheter shaft 80 and coupled to electrode wire 90. Distal end 82 is sharpened to facilitate penetration of tissue in conjunction with electrode 92.

At proximal end 84, shaft 80 is mounted to a connector 94 having a luer fitting 96 and an electrosurgical plug 98.

Fitting 96 is in communication with first shaft passage 86 via a passage 100 to provide fluid connection with an infusion fluid delivery device. Electrosurgical plug is coupled to electrode wire 90 and may be connected to an electrosurgical power supply. Alternatively, an electrosurgical connector 34 as described above may be used, whereby electrode wire 90 is coupled to luer fitting 96, constructed of a conductive material, so that luer fitting 96 provides both fluid connection to a fluid delivery device as well as electrical connection to a power supply.

The infusion catheter of the present invention derives significant advantage from its self-introducing capabilities. The device may be percutaneously introduced, for example, through the abdominal wall, by direct penetration of tissue, without the use of separate needles, obturators, cannulas or other introduction instruments. This is achieved by applying energy to tissue through electrode 28 at the distal end of catheter body 22 with sufficient power and intensity to ablate and penetrate the tissue. In a preferred embodiment, the catheter will be connected via electrosurgical connector 34 to an electrosurgical power supply. Usually, the electrosurgical power supply will be a radiofrequency (RF) power generator, but may also comprise an ultrasonic generator or other suitable power supply. The power supply must deliver energy to electrode 38 sufficient to cause ablation of tissue to facilitate penetration. An RF power generator used in conjunction with the infusion catheter of the present invention will preferably deliver power of at least 20 watts.

Figure 5A:
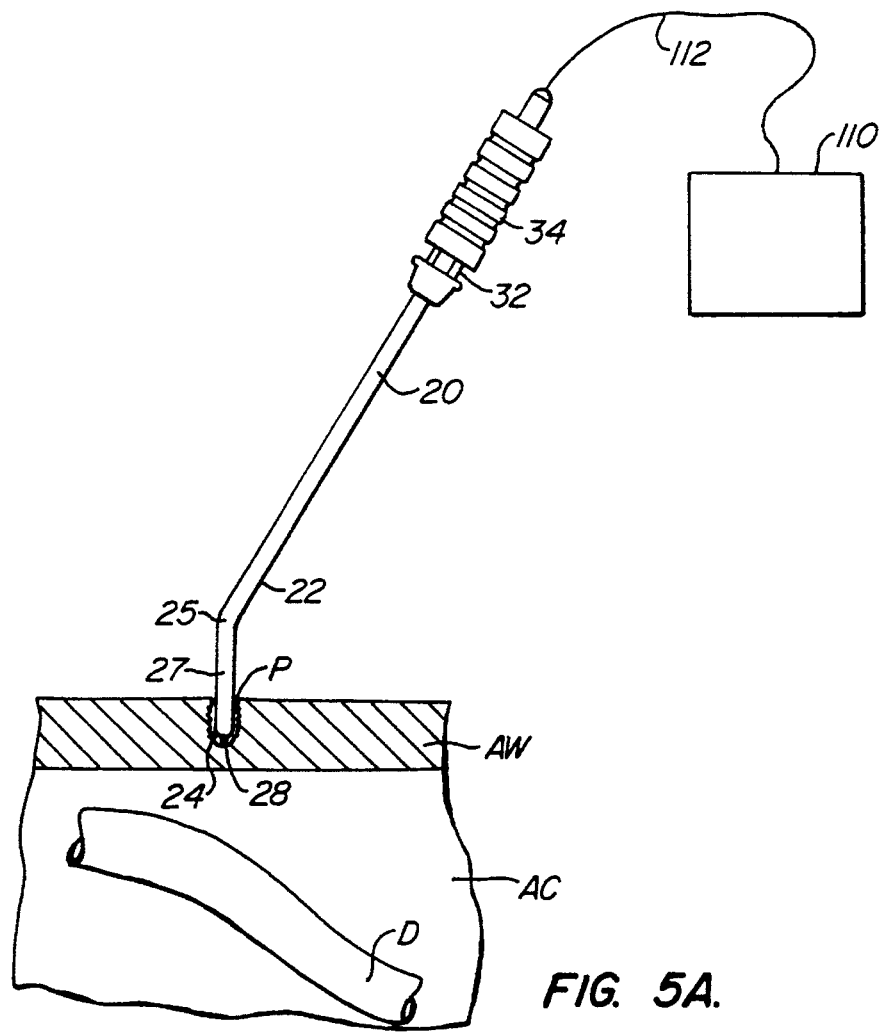
FIGS. 5A–5D are side views of the self-introducing infusion catheter of FIG. 1 in use according to the method of the present invention.
Figure 5B:
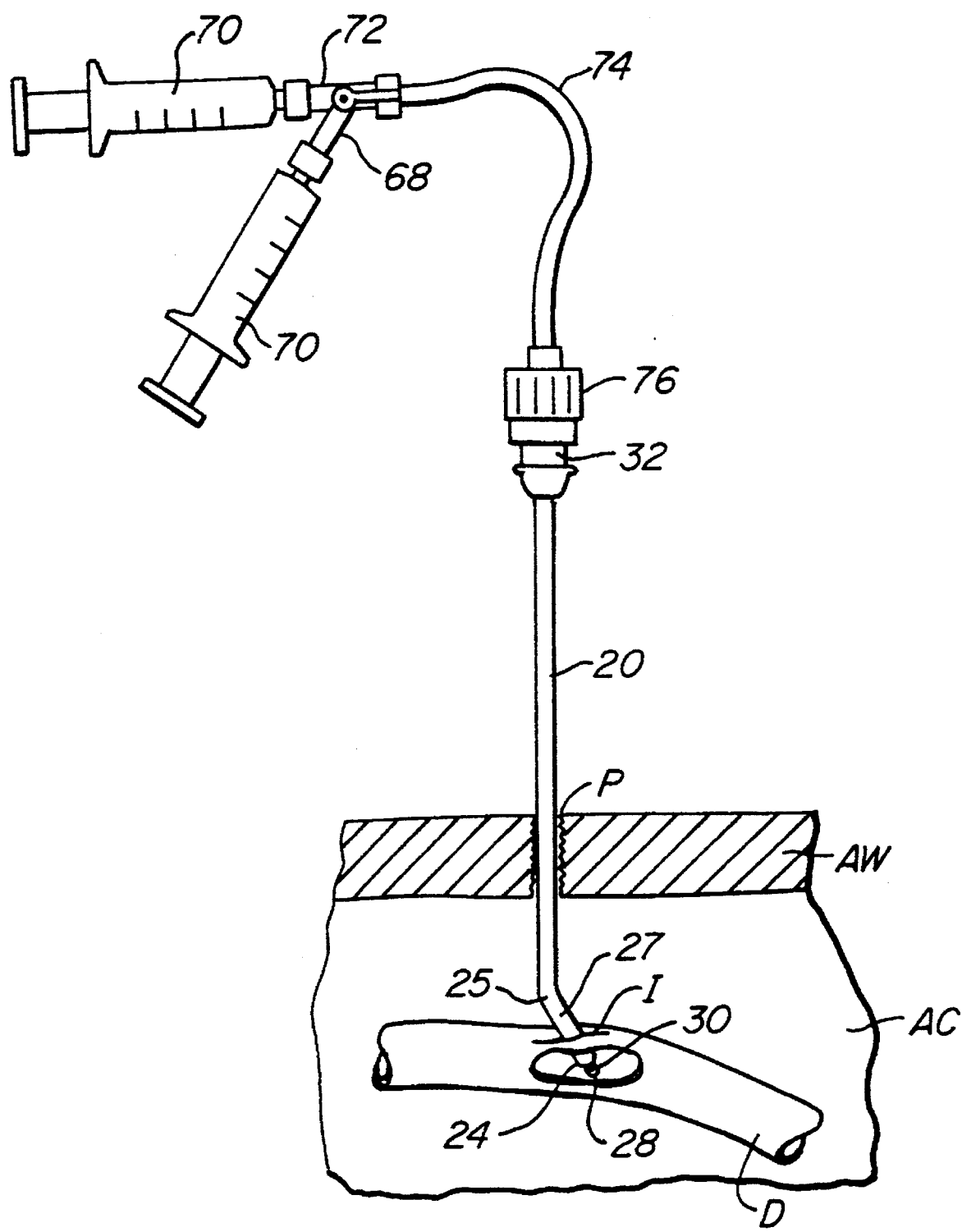
Figure 5C:
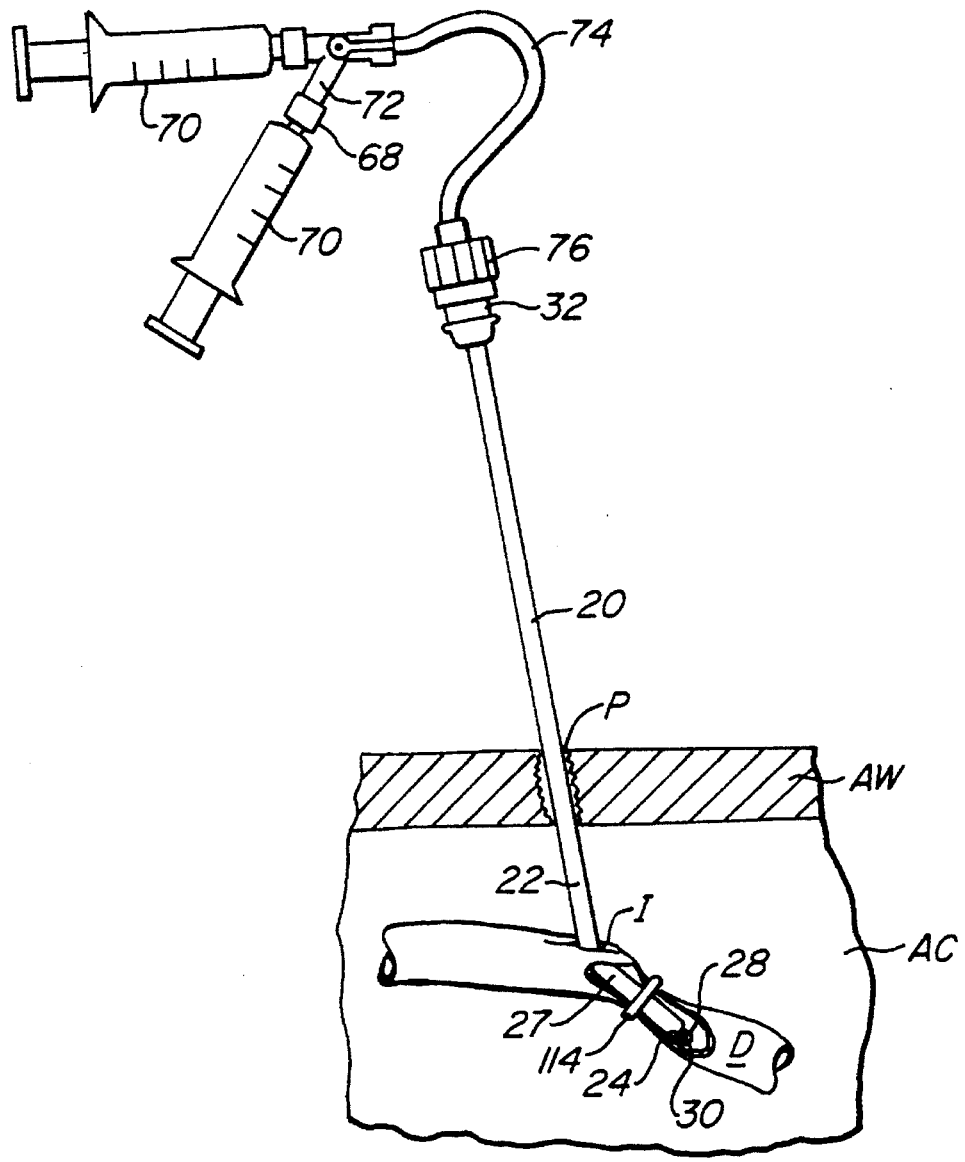

A preferred embodiment of the method of the present invention is illustrated in FIGS. 5A–5D. As shown in FIG. 5A, connector 32 of catheter 20 is connected to electrosurgical connector 34, which is coupled via conductor 112 to an electrosurgical power supply 110. Electrosurgical power supply 110 will preferably comprise an RF generator. The distal end 24 of catheter 20 is positioned at the desired site of introduction into the body. For cholangiography, the catheter will be introduced through the abdominal wall AW in order to gain access to the cystic duct D in the abdominal cavity AC. Electrosurgical power supply 110 is then activated such that power is supplied to electrode 28 at distal end 24. Electrode 28 applies ablative energy to the tissue of abdominal wall AW, while a distal force is applied to the catheter by the user gripping the exterior of electrosurgical connector 34. A penetration p through abdominal wall AW is formed through which catheter shaft 22 may pass.

As illustrated in FIG. 5B, catheter 20 is positioned within abdominal cavity AC so that distal end 24 is within duct D. Usually, distal end 24 will be inserted through an incision I in duct D which is made using separate instruments. Alternatively, electrode 28 may be used to ablate the wall tissue of the duct so as to penetrate the duct in the manner used for introduction through abdominal wall AW.

When distal end 24 is positioned in duct D, the electrosurgical connector 34 may be disconnected from catheter connector 32, and an infusion fluid delivery device 68 may be connected. In an exemplary embodiment, the infusion fluid delivery device will include two syringes 70 connected by a 3-way stopcock valve 72 to a connection line 74 having a fitting 76 at its end. Fitting 76 is coupled to catheter connector 32 to establish fluid connection. In cholangiography, a contrast medium will be contained in syringes 70. Typically, the contrast medium will comprise a mixture of saline solution contained in one syringe 70 and contrast dye contained in the second syringe 70.

Figure 5D:
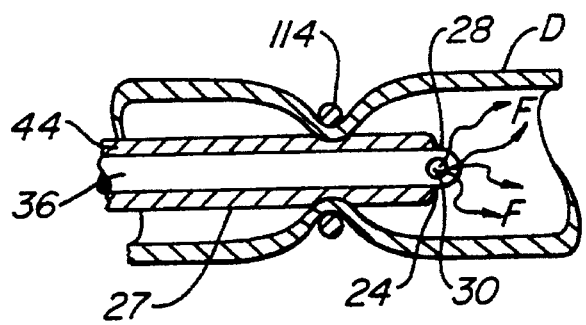

Referring to FIG. 5C, catheter 20 is positioned through incision I with a distal portion 27 of the catheter within duct D. This is facilitated by the bend 25 in shaft 22 which allows alignment of distal portion 27 with the geometry of duct D. A clip 114 is then applied about the perimeter of duct D and tightly clamped to seal the interior of duct D against the exterior of sleeve 44 of the catheter. A conventional surgical clip applier of well-known construction such as that described in U.S. Pat. No. 3,777,538, the complete disclosure of which is incorporated herein by reference, may be used for this purpose. By sealing off the duct D at the clip 114, the contrast medium may be infused into the duct in a desired direction and will be prevented form leaking back through incision I. As illustrated in FIG. 5D, clip 114 is preferably applied with sufficient force to compressively deform sleeve 44 in distal portion 27 of the catheter. This secures the catheter in the duct to prevent movement during the procedure, as well as ensures a tight seal between the duct D and sleeve 44.

Finally, contrast medium F is delivered from fluid delivery device 68 and infused into duct D through infusion ports 30.

Although the foregoing invention has been described in detail for purposes of clarity of understanding, it will be obvious that certain modifications may be practiced within the scope of the appended claims.

What is claimed is:

1. A method of introducing a fluid into a lumen of a body duct, the method comprising:

percutaneously introducing a catheter through body tissue into the lumen by applying ablative energy to said tissue through an electrode disposed at the distal tip of the catheter to form an opening in a wall of the duct;

positioning a distal portion of the catheter through said opening in the wall of the duct such that an infusion port in the distal portion of the catheter lies in the lumen of the duct;

applying a clip about the duct with the distal portion of the catheter positioned therein to seal the lumen around the catheter, the clip being applied so as to compressively deform a sleeve about the distal portion of the catheter to secure the catheter in position in the lumen; and infusing a fluid into the duct through the infusion port.

2. A method as in claim 1 wherein the energy is radiofrequency energy.

3. A method as in claim 1 wherein the body duct is the cystic duct and the fluid is a contrast medium.

4. A method as in claim 1 wherein the catheter is introduced through the abdominal wall into the abdominal cavity.

5. A method as in claim 1 wherein energy is applied to a proximal end of a rigid electrically conductive shaft extending longitudinally through the catheter, the distal tip of the shaft comprising the electrode.

6. A method as in claim 5 wherein the fluid is introduced into a proximal end of a passage extending longitudinally through the shaft to the infusion port.

7. A method as in claim 1 wherein the opening in the duct is made by penetrating through the wall of the duct with the distal end of the catheter by applying ablative energy through the electrode.

8. A self-introducing infusion catheter comprising:

a rigid, elongate catheter body having a distal end, a proximal end and a passage therebetween, wherein said catheter body has sufficient column strength so that it will not significantly deflect when an axially directed force is applied to penetrate tissue;

an infusion port near the distal end in communication with the passage;

an electrode disposed at the distal end for applying ablative energy to tissue;

means at the distal end of the catheter body to facilitate penetration of the infusion port through tissue ablated by the electrode, the penetration means comprising a sharpened edge on the distal end of the catheter body;

means at the proximal end of the catheter body for introducing fluid into the passage; and means at the proximal end of the catheter body for selectively connecting the electrode to an energy source.

9. An infusion catheter according to claim 8 wherein the catheter body has a second passage for housing an electrode wire, the electrode wire being coupled to the electrode at the distal end and to the connecting means at the proximal end.

10. An infusion catheter according to claim 8 wherein the catheter body is electrically insulating.

11. An infusion catheter according to claim 8 wherein the distal end of the catheter body is chamfered to define the sharpened edge, with the electrode disposed at the distal edge of the chanfered surface.

* * * * *